(12) United States Patent
Roberts

(10) Patent No.: US 8,662,705 B2
(45) Date of Patent: Mar. 4, 2014

(54) FLEXIBLE ULTRAVIOLET LED SANITIZING APPARATUS

(75) Inventor: Jon L. Roberts, Great Falls, VA (US)

(73) Assignee: Virwall Systems, Inc., Lakeville, CT (US)

( * ) Notice: Subject to any disclaimer, the term of this patent is extended or adjusted under 35 U.S.C. 154(b) by 731 days.

(21) Appl. No.: 12/749,802

(22) Filed: Mar. 30, 2010

(65) Prior Publication Data

US 2011/0243789 A1 Oct. 6, 2011

(51) Int. Cl.
F21L 2/00 (2006.01)

(52) U.S. Cl.
USPC .......... 362/249.04; 362/249.02; 362/545; 422/24

(58) Field of Classification Search
USPC ........ 422/24, 186.3; 362/249.04, 249.02, 545
See application file for complete search history.

(56) References Cited

U.S. PATENT DOCUMENTS

| | | |
|---|---|---|
| 3,954,407 A | 5/1976 | Andary et al. |
| 3,955,922 A | 5/1976 | Moulthrop |
| 4,088,445 A | 5/1978 | Ellis |
| 4,100,415 A | 7/1978 | Blaisdell et al. |
| 4,625,119 A | 11/1986 | Murdock, III |
| 4,694,180 A | 9/1987 | Salisbury et al. |
| 4,772,795 A | 9/1988 | Sakurai et al. |
| 4,793,507 A | 12/1988 | Delplanque |
| 4,803,364 A | 2/1989 | Ritter |
| 4,806,770 A | 2/1989 | Hylton et al. |
| 4,888,487 A | 12/1989 | Ritter |
| 4,906,851 A | 3/1990 | Beasley |
| 4,973,847 A | 11/1990 | Lackey et al. |
| 5,008,933 A | 4/1991 | Kao et al. |
| 5,023,460 A | 6/1991 | Foster, Jr. et al. |
| 5,126,572 A | 6/1992 | Chu |
| 5,127,521 A | 7/1992 | Bourque |
| 5,225,172 A | 7/1993 | Meyler et al. |
| 5,396,557 A | 3/1995 | Tonci |
| 5,487,877 A | 1/1996 | Choi |
| 5,547,635 A | 8/1996 | Duthie, Jr. |
| 5,588,549 A | 12/1996 | Furtner |
| 5,979,472 A | 11/1999 | Lowery et al. |

(Continued)

FOREIGN PATENT DOCUMENTS

| | | |
|---|---|---|
| AU | 764360 B2 | 8/2003 |
| AU | 768839 B2 | 1/2004 |

(Continued)

OTHER PUBLICATIONS

International Search Report, Intl. Application PCT/US99/01597 (PCT Publication WO 99/38540). WIPO (ISA/EP), Jun. 10, 1999, 7 pages.

(Continued)

Primary Examiner — Sean E Conley
(74) Attorney, Agent, or Firm — The Marbury Law Group, PLLC

(57) ABSTRACT

A sanitizing apparatus in a flexible configuration that uses ultraviolet (UV) radiation emitted from light emitting diodes (LEDs) may be folded or rolled for storage and transport. A piecewise flexible sanitizing apparatus may be formed with hinged or otherwise rotationally joined panels, and provides the ability to sanitize a variety of objects beneath enclosure panels. A continuous flexible sanitizing apparatus with an enclosure panel formed of flexible material may be folded or rolled and may be used with a support structure to treat taller objects.

16 Claims, 7 Drawing Sheets

(56) References Cited

U.S. PATENT DOCUMENTS

| | | | |
|---|---|---|---|
| 6,030,099 | A | 2/2000 | McDermott |
| 6,039,928 | A | 3/2000 | Roberts |
| D434,613 | S | 12/2000 | Tramontina |
| 6,278,122 | B1 | 8/2001 | Gagnon |
| 6,301,359 | B1 | 10/2001 | Roberts |
| 6,365,113 | B1 | 4/2002 | Roberts |
| 6,458,331 | B1 | 10/2002 | Roberts |
| 6,490,351 | B1 | 12/2002 | Roberts |
| D502,546 | S | 3/2005 | Shin |
| 6,974,223 | B2 | 12/2005 | Krietzman |
| D542,929 | S | 5/2007 | Shin |
| 7,273,300 | B2 | 9/2007 | Mrakovich |
| D573,474 | S | 7/2008 | Beam et al. |
| D584,417 | S | 1/2009 | Massee |
| D593,262 | S | 5/2009 | Gong |
| D616,563 | S | 5/2010 | Huck et al. |
| 7,825,325 | B2 * | 11/2010 | Kennedy et al. ............. 136/244 |
| 8,177,383 | B2 * | 5/2012 | Reuben ........................ 362/103 |
| 8,197,087 | B2 * | 6/2012 | Sobue et al. ............ 362/249.02 |
| 2003/0048256 | A1 | 3/2003 | Salmon |
| 2008/0265179 | A1 | 10/2008 | Havens et al. |
| 2012/0182755 | A1 * | 7/2012 | Wildner ....................... 362/555 |

FOREIGN PATENT DOCUMENTS

| | | |
|---|---|---|
| BE | 531883 | 12/1957 |
| CA | 2316086 C | 2/2002 |
| CA | 2365306 C | 1/2005 |
| CA | 2359477 C | 7/2005 |
| DE | 297 20 530 U1 | 1/1998 |
| DE | 10332771 A1 * | 3/2005 |
| EP | 1051199 B1 | 7/2009 |
| EP | 0493372 A2 | 6/2010 |
| FR | 2631-240 A2 | 11/1989 |
| GB | 2363332 B | 4/2003 |
| GB | 2363281 B | 8/2003 |
| GB | 2383225 B | 8/2003 |
| JP | 61-012769 A | 1/1986 |
| JP | 04-364644 A | 12/1992 |
| JP | 07-160362 A | 6/1995 |
| JP | 07-329481 A | 12/1995 |
| JP | 08-025876 A | 1/1996 |
| MX | 230716 | 9/2005 |
| MX | 254252 | 2/2008 |
| NZ | 513043 | 3/2003 |
| NZ | 513044 | 7/2003 |
| WO | 95/28181 A1 | 10/1995 |
| WO | 99/26668 A1 | 6/1999 |
| WO | 99/38540 A1 | 8/1999 |
| WO | 00/06209 A2 | 2/2000 |
| WO | 00/41734 A1 | 7/2000 |
| WO | 01/41733 A1 | 7/2000 |
| WO | 01/51098 A1 | 7/2001 |
| WO | 01/70280 A1 | 9/2001 |

OTHER PUBLICATIONS

International Preliminary Examination Report, Intl. Application PCT/US99/01597 (PCT Publication WO 99/38540). WIPO (IPEA/US), Oct. 28, 1999, 10 pages.
International Search Report, Intl. Application PCT/US00/00448 (PCT Publication WO 00/41733). WIPO (ISA/EP), May 24, 2000, 6 pages.
Written Opinion, Intl. Application PCT/US00/00448 (PCT Publication WO 00/41733). WIPO (ISA/EP), Mar. 16, 2001, 6 pages.
Response to Written Opinion, Intl. Application PCT/US00/00448 (PCT Publication WO 00/41733). Filed May 11, 2001, 8 pages.
International Preliminary Examination Report, Intl. Application PCT/US00/00448 (PCT Publication WO 00/41733). WIPO (IPEA/US), Jul. 27, 2001, 8 pages.
International Search Report, Intl. Application PCT/US00/00547 (PCT Publication WO 00/41734). WIPO (ISA/EP), May 24, 2000, 3 pages.
International Preliminary Examination Report, Intl. Application PCT/US00/00547 (PCT Publication WO 00/41734). WIPO (IPEA/US), Jul. 12, 2001, 14 pages.
International Search Report, Intl. Application PCT/US01/01169 (PCT Publication WO 01/51098). WIPO (ISA/EP), Jun. 12, 2000, 3 pages.
International Search Report, Intl. Application PCT/US01/08665 (PCT Publication WO 01/70280). WIPO (ISA/EP), Aug. 16, 2000, 3 pages.
International Preliminary Examination Report, Intl. Application PCT/US01/08665 (PCT Publication WO 01/70280). WIPO (IPEA/US), Jul. 2002, 7 pages.
International Search Report and Written Opinion, Intl. Application PCT/US10/29935. WIPO (ISA/US),Jun. 3, 2010, 13 pages.
Examiner's Report, Australian Application 24966/00 (now Australian Patent 764360). IP Australia, Feb. 25, 2002, 2 pages.
Response to Examiner's Report, Australian Application 24966/00 (now Australian Patent 764360). Apr. 9, 2003, 18 pages.
Examiner's Report, Australian Application 24985/00 (now Australian Patent 768839). IP Australia, Feb. 25, 2002, 3 pages.
Response to Examiner's Report, Australian Application 24985/00 (now Australian Patent 768839). Oct. 30, 2003, 3 pages.
Office Action, European Application 99904277.3 (now European Patent 1051199). European Patent Office, Apr. 26, 2004, 5 pages.
Response to Office Action, European Application 99904277.3 (now European Patent 1051199). Aug. 26, 2004, 7 pages.
Office Action, European Application 99904277.3 (now European Patent 1051199). European Patent Office, Jul. 28, 2006, 3 pages.
Response to Office Action, European Application 99904277.3 (now European Patent 1051199). Nov. 16, 2006, 8 pages.
Interview Summary, European Application 99904277.3 (now European Patent 1051199). European Patent Office, Oct. 16, 2007, 3 pages.
Response to Interview Summary, European Application 99904277.3 (now European Patent 1051199). Feb. 7, 2008, 18 pages.
Examination Report, United Kingdom Application 0119651.8 (now GB Patent 2363281). United Kingdom Patent Office, Aug. 27, 2002, 4 pages.
Response to Examination Report, United Kingdom Application 0119651.8 (now GB Patent 2363281). Feb. 27, 2003, 24 pages.
Examination Report, United Kingdom Application 0119651.8 (now GB Patent 2363281). United Kingdom Patent Office, Apr. 15, 2003, 2 pages.
Response to Examination Report, United Kingdom Application 0119651.8 (now GB Patent 2363281). Jun. 19, 2003, 13 pages.
Examination Report, United Kingdom Application 0304495.5 (now GB Patent 2383225). United Kingdom Patent Office, Apr. 14, 2003, 4 pages.
Response to Examination Report, United Kingdom Application 0304495.5 (now GB Patent 2383225). United Kingdom Patent Office, Jun. 19, 2003, 15 pages.
Translation of Office Action, Mexican Application PA/a/2001/007050 (now Mexican Patent 230716). Mexican Institute of Industrial Property, Mar. 19, 2005, 2 pages.
Letter to Uhthoff, Gomez Vega & Uhthoff from Roberts Abokhair & Mardula LLC, with instructions for response to Examination Report, Mexican Application PA/a/2001/007050 (now Mexican Patent 230716). Apr. 11, 2005, 3 pages.
Response to Office Action, Mexican Application PA/a/2001/007050 (now Mexican Patent 230716). May 10, 2005, 5 pages.
Translation of Office Action, Mexican Application Pa/a/2001/007048 (now Mexican Patent 254252). Mexican Institute of Industrial Property, Oct. 2, 2007, 2 pages.
Response to Office Action, Mexican Application PA/a/2001/007048 (now Mexican Patent 254252). Dec. 11, 2007, 14 pages.
Examination Report, New Zealand Application 513044 (now New Zealand Patent 513044). Intellectual Property Office of New Zealand, Mar. 13, 2002, 2 pages.
Response to Examination Report, New Zealand Application 513044 (now New Zealand Patent 513044). Oct. 22, 2002, 13 pages.

(56) References Cited

OTHER PUBLICATIONS

Examination Report, New Zealand Application 513044 (now New Zealand Patent 513044). Intellectual Property Office of New Zealand. Nov. 8, 2002, 2 pages.

Response to Examination Report, New Zealand Application 513044 (now New Zealand Patent 513044). Jan. 10, 2003, 2 pages.

International Preliminary Report on Patentability issued in PCT Application PCT/US2010/029935, mailed on Oct. 13, 2011.

* cited by examiner

FLEXIBLE ULTRAVIOLET LED SANITIZING APPARATUS

FIELD OF THE INVENTION

The various embodiments relate generally to the sanitization of various surfaces, and more particularly to methods, materials and apparatus utilizing ultraviolet light to effectively reduce microbe levels.

BACKGROUND

It has long been known that germs are spread by, among other things, hand to hand contact. Hence, recent public health campaigns and media have emphasized the importance of washing of hands in order to prevent the spreading of the common cold as well as other pathogens. Further, it has long been known that household objects such as toothbrushes can be a source of the spreading of germs as well, and recent discovery has shown that bacteria continue to live on writing implements that are used by individuals. Disease-causing germs can live on many surfaces and therefore can be a vector for the spread of disease.

SUMMARY

Hospitals routinely sanitize surgical instruments, which typically involves both the use of chemicals as well as high-pressure high-temperature steam such as is produced in an autoclave machine. This results in generally sterile instruments for use in surgery (i.e., maximum elimination of microbes). Such devices, however, are expensive, cumbersome, and are therefore not practical for the widespread sanitizing of more common devices that do not require a sterile field.

Common household disinfectants for kitchen and bathroom surfaces, toys, and other objects traditionally rely on chemicals such as alcohols, aldehydes, and oxidizing agents. However, most disinfectants are also by nature potentially harmful (even toxic) to humans or animals. Further, the introduction of a harsh chemical substance to a device with electrical components has the potential to damage the internal systems thereof.

It would therefore be desirable to have a convenient sanitizing method and apparatus for sanitizing many different kind of objects and surfaces, including keyboards and other input devices of all types and dimensions (collectively "computer input device(s)") thereby preventing the transmission of object-borne disease spreading microorganisms. Such devices would benefit schools, health care facilities, offices, and retail environments, as well as other places where frequently used objects are susceptible to high germ transmission.

DESCRIPTION OF THE DRAWINGS

The accompanying drawings, which are incorporated herein and constitute part of this specification, illustrate exemplary aspects of the invention. Together with the general description given above and the detailed description given below, the drawings serve to explain features of the invention.

DETAILED DESCRIPTION

Figure 1:
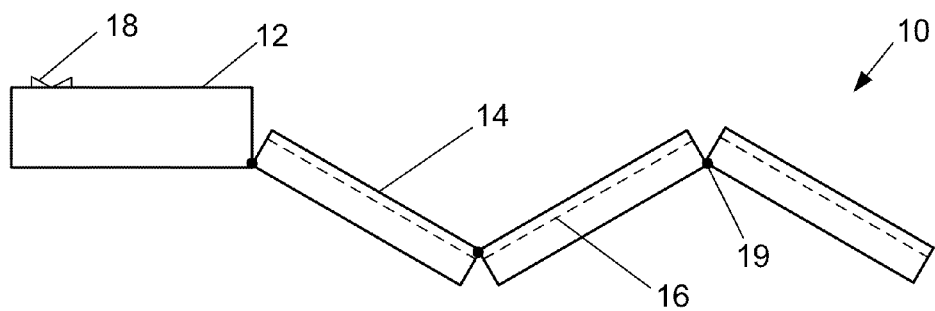
FIG. 1 illustrates a side elevation view of a horizontally disposed sanitizing apparatus with hinged panels according to an embodiment.

Ultraviolet (UV) radiation is known as a highly effective means of destroying microorganisms. At an optimal wavelength of 254 nm, shortwave UV radiation (UVC) exposure kills bacteria, molds, protozoa, yeasts, and viruses on the surfaces of household and personal objects, eliminating over 99% of surface microbes. Exposure to UVC damages microbial DNA by triggering adjacent thymine molecules to dimerize, thereby disrupting DNA and RNA replication and ultimately killing the pathogen.

The application of UVC radiation to sanitization has been used extensively in medical sterilization of flat surfaces, water treatment and air purification, and in recent years, household surface sanitization applications. Commercially available germicidal UV lamps are hand-held ("wands") and operate using incandescent or fluorescent UVC bulbs. However, there are many limitations to the use of currently available UV light wands. Such devices give non-uniform exposure since the user "waves" the light over the surface. Each user is different and yields a different level of efficacy. Further, there is a concern with respect to UVC exposure to users and bystanders since UVC radiation more damaging to human eyes and more carcinogenic to skin than UVA and UVB radiation.

The use of light emitting diodes (LEDs) in a sanitizing apparatus provides several advantages over incandescent and fluorescent bulbs and provides the ability to create a broad range of sanitizers with flexibility to treat a variety of objects and surfaces. Additionally, LEDs do not have filaments that can burn out thus lasting longer, and the small plastic bulbs of LEDs make them more durable and able to fit more easily into modern electronic circuits.

Another advantage to the use of LEDs is efficiency of power usage, as a conventional incandescent bulb, in warming the filament, generates a good amount of wasted energy in the form of heat. The various embodiment apparatus and methods utilize LEDs to generate UVC in a range of flexible configurations that are easy and safe to use and that surpass the performance of currently available UV-emitting sanitizing devices. Treatment of a surface according to the various embodiments has kill rates of over 99.99% of bacteria and influenza virus, accomplished in under 60 seconds.

The various aspects will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The terms "UVC", "UVC light" and "UVC radiation" are used interchangeably herein consistent with customary application in physics to refer to ultraviolet electromagnetic radiation having a wavelength of 100 nm-280 nm.

FIG. 1 illustrates an embodiment sanitizing apparatus 10 that includes a plurality of panels 14, thus creating a piecewise flexible configuration Each panel 14 contains a two-dimensional array of UV-emitting LEDs 16, and such LEDs that emit disinfecting UVC radiation in the 254 nm and lower wavelength range. The panels 14 may be attached to each other and to electrical control box 12 with hinges 19 such that the apparatus 10 is piecewise flexible at the hinges. Such hingeadly flexible configuration enables the apparatus 30 to fold into a compact storage/transport arrangement and unfold for use. An elongated apparatus 10 as shown in FIG. 1 is suitable for sanitizing elongated areas such as a keyboard surface for a computer, typewriter, ATM, musical instrument, etc. Each panel 14 forms an opaque enclosure with an open side that allows the array of UV LEDs 16 to treat an object. In order to protect the UV LED arrays 16 and prevent possible accidental exposure to UVC radiation, it is preferable that the panels 14 fold in such a manner such that so as to not have the arrays 16 exposed, although this is not a limitation.

Figure 2:
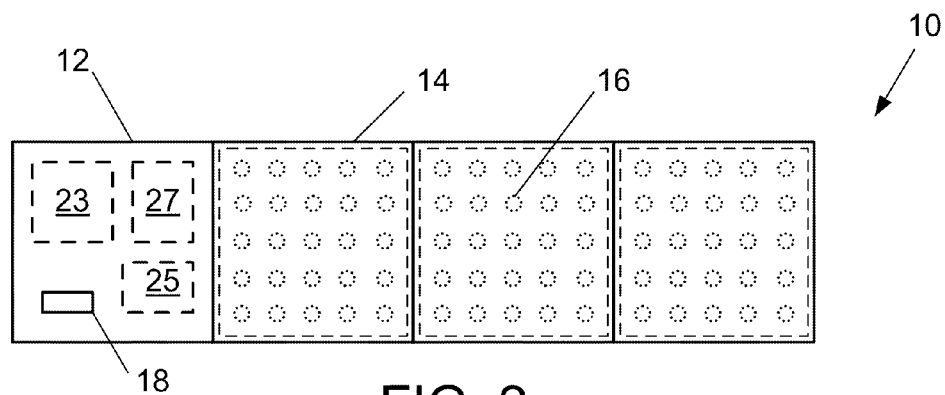
FIG. 2 illustrates a top plan view of the sanitizing apparatus with hinged panels in FIG. 1.

FIG. 2 illustrates a top view of sanitizing apparatus 10 in an unfolded operational position. After being unfolded, the apparatus 10 may be placed over the item to be sanitized and switch 18 may be activated to operate the UV LEDs 16 and thus sanitize the item. Control box 12 may include an activation switch 18 and a power source 23 that may be any source suitable for electrically powering the plurality of LEDs 16, including, but not limited to, an AC power cord and appropriate transformer, a DC power cord from a "wall wort" transformer or battery pack, a USB or IEEE 1394 receptacle for plugging into a (DC) powered USB or IEEE 1394 device, a battery or set of batteries (e.g., LiPo, alkaline, Ni-Cad, etc.), or a fuel cell (e.g., using methanol, butane or formic acid). Control box 12 may additionally include a timing unit or circuit 25 to control the duration of sanitization, as well as an interlock control circuit 27 to prevent accidental operation of the apparatus 10 and possible exposure to dangerous UVC radiation from the LEDs. Interlock control circuit 27 may coordinate one or more switches that are normally biased in the off position until the apparatus is opened and positioned over an object to be treated. See, e.g., U.S. Pat. No. 6,458,331, which is herein incorporated by reference. Optionally, a horizontally-disposed apparatus, for example, as illustrated in FIG. 2, may include a level switch (not shown) in the control box as a safety means to inhibit operation of the apparatus if the panels are not aligned in a level horizontal position. Such level switch may be, but is not limited to, a mercury tilt switch, a roller ball, or a magnetic switch.

An interlock switch may be used to turn units on or off, it is preferable to include a separate activation switch 18 for embodiments that are powered by AC, DC, battery or fuel cell. Optionally, the activation switch 18 may further include a light or other indicator to signal that the UV LEDs are operating, or the control box 12 may further include a timed circuit with different lights or other indicators, each of which may show that the sanitizing apparatus is either ready for operation, currently operating, or that sanitization is complete. The sanitizing time is set so as to deliver the appropriate amount of UV energy needed to deactivate a range of micro-organism. Tables of energy for deactivation of a variety of micro-organisms is readily available to those skilled in the art. Noted below are some examples of the amount of UV energy levels at 254 nanometer units wavelength in microwatt-seconds per square centimeter required for 99.9% destruction of various organisms as but some examples, without limitation, or organisms that can be destroyed with various embodiments illustrated herein.

Virus
Coliphage 6,600
Hepatitis virus (infectious) 8,000
Influenza virus 6,600
Poliomyelitis (polio virus) 21,000
Rotavirus 24,000
Tobacco mosaic virus 440,000
Bacterial Organisms
*Agrobacterium tumefaciens* 8,500
*Bacillus anthracis* 8,700
*B. megaterium* (vegetable) 2,500
*B. megaterium* (spores) 52,000
*B. paratyphosus* 6,100
*B. subtilis* (vegetable) 11,000
*B. subtilis* (spores) 22,000 *Escherichia coli* 6,600
*Legionella bozemanii* 3,500
*L. dumoffii* 5,500
*L. gormanii* 4,900
*L. longbeachae* 2,900
*L. micdadel* 3,100
*L. pneumophila* 3,800

Sanitizing apparatus 10 may optionally contain one or more additional two-dimensional arrays of UV-emitting LEDs facing an open side of one or more additional enclosure panels in which the additional arrays are mounted, with an additional hinge rotationally connecting the additional panels to one of the first and the second panel enclosure to allow the additional panel to rotate from a storage position to an operational position.

Figure 3:
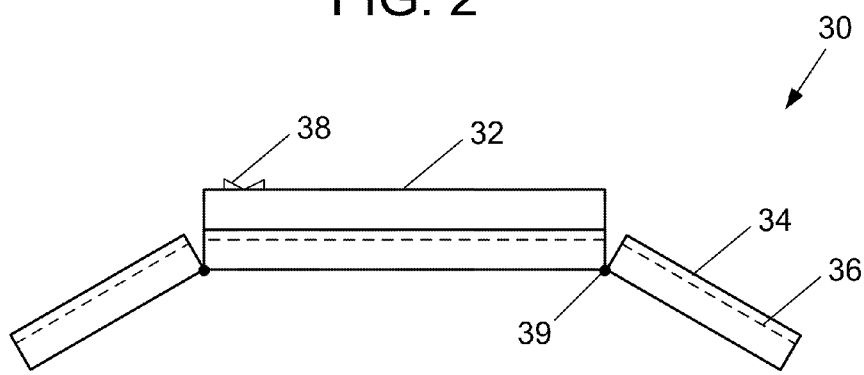
FIG. 3 illustrates a side elevation view of a horizontally disposed sanitizing apparatus with hinged panels according to an alternative embodiment.

FIG. 3 illustrates an alternative embodiment in which enclosure panels form a piecewise flexible configuration. The apparatus 30 has a control box 32 and an activation switch 38 that are integrated with one of the panels 34. The panels 34 include two-dimensional arrays of UV LEDs 36 and may be attached by hinges 39, enabling the hingeably flexible apparatus 30 to fold into a compact storage/transport arrangement and unfold for use. A center panel may be integrated with the control box 32, as is illustrated, and may be approximately twice the width of the outer panels such that the outer panels can fold inward to protect the center array.

Figure 4A:
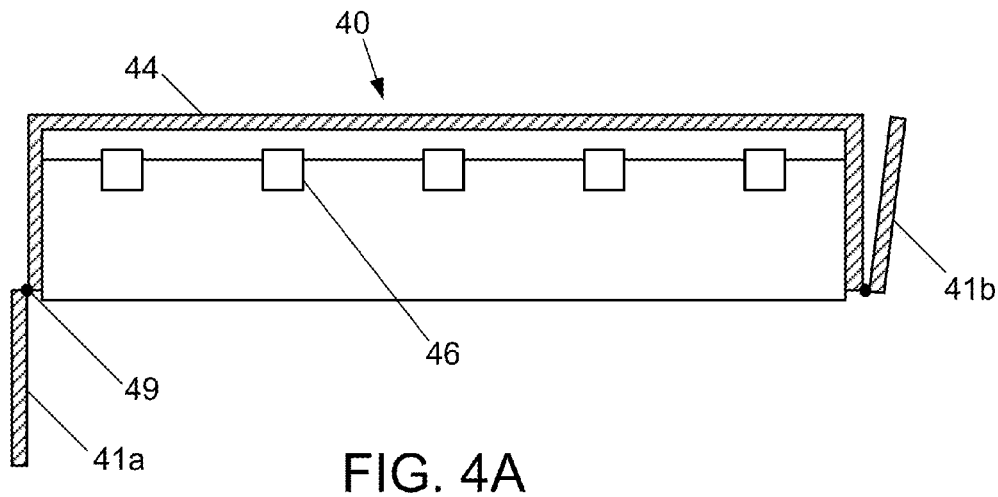
FIGS. 4A and 4B illustrate cross-sectional views of a panel of a horizontally disposed sanitizing apparatus showing storage and operational configurations according to various embodiments.
Figure 4B:
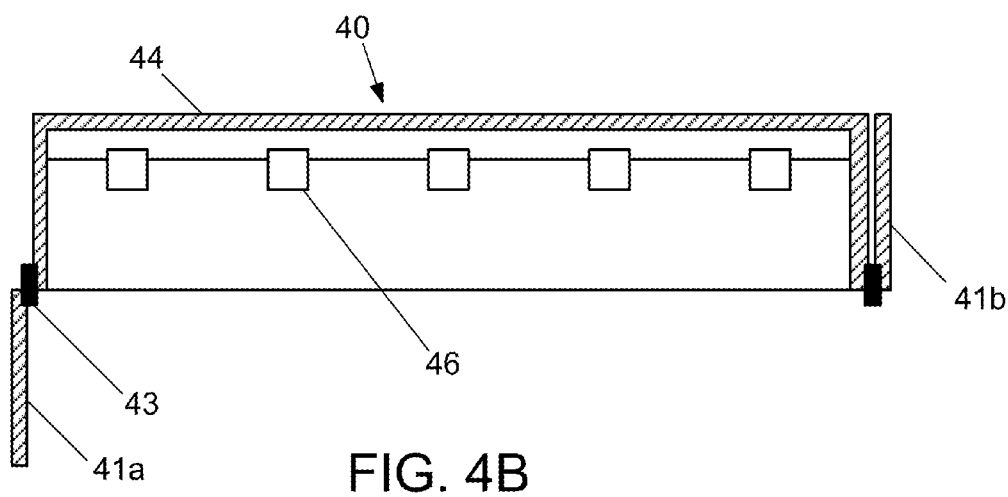

When unfolded, the panels 14 of FIGS. 1 and 2 and panels 34 of FIG. 3 form an open-sided enclosure for treating an object with UVC radiation. While using folding panels in an embodiment apparatus forms a compact unit for storage and transport, the panels may conversely be designed so as to have sufficient height to enclose the objects to be treated. FIGS. 4A and 4B illustrate variations of an embodiment in which panels have side-wall fixtures providing increased enclosure height while still allowing compact storage. Referring to FIG. 4A, an apparatus 40 may contain one or more enclosure panels 44 in which a two-dimensional array of UV LEDs 46 is mounted adjacent the opaque face of each the enclosure panel 44. The side-walls of the enclosure panels 44 include extensions 41a, 41b, which may be attached by hinges 49 so as to move between the storage position of extension 41b and the extended position of extension 41a.

FIG. 4B illustrates an alternative configuration of extensions 41a, 41b. In this example configuration, extensions 41a, 41b may be slidably attached by guides 43 so as to move between the storage position of extension 41b and the operational position of extension 41a. The use of side extensions 41a, 41b may allow the sanitizing apparatus 40 to fold more compactly, the treatment of taller objects, and the use of fewer LEDs or LEDs with narrower projection angles.

Figure 5A:
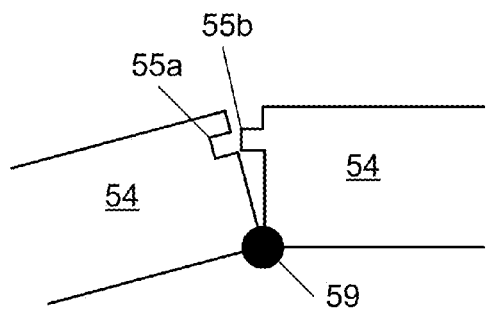
FIGS. 5A and 5B illustrate detailed side elevation views of an interlock element illustrating the connectivity for operation of a sanitizing apparatus according to various embodiments.
Figure 5B:
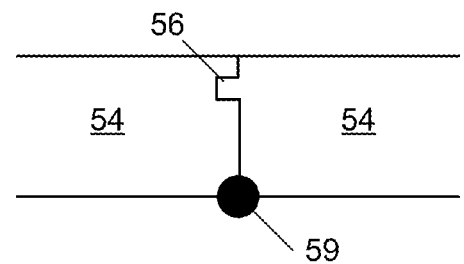

As discussed above, various embodiments may have safety and/or interlock switching means to prevent unintended operation of a sanitizing apparatus that generates UVC radiation, such as when in a folded storage configuration. FIGS. 5A and 5B illustrate an exemplary embodiment of an interlock mechanism within a piecewise flexible apparatus by which operation of panels 54 may be prevented when the sanitizing apparatus is in a folded position. FIG. 5A illustrates two enclosure panels 54 that are joined by a hinge 59 so as to allow the panels 54 to be folded into a storage position. Interlock elements 55a, 55b may be any suitable means for completion of a circuit capable of energizing the UV LEDs, (for example, mating electrical contacts) and such elements are in a nonoperational position when the panels 54 are folded. However, when panels 54 are rotated about the hinge 59 to a position for active use, as shown in FIG. 5B, the interlocking elements may form an operational position 56 (for example, as a completed electrical contact) thus allowing operation of the panels, assuming other interlock elements are also in proper position.

Figure 6:
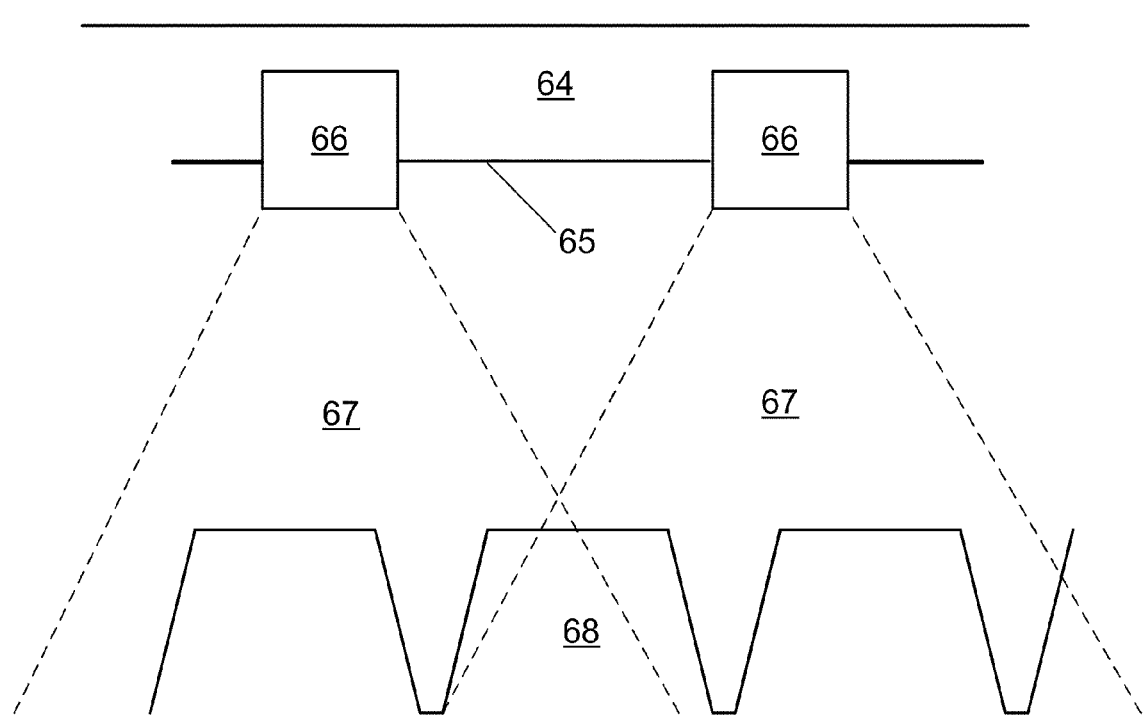
FIG. 6 illustrates a schematic detail view of light emitting diodes illustrating emittance of ultraviolet radiation in treating the surface of an object.

FIG. 6 illustrates the operation of individual UV LEDs 66 illuminating an object 68 (e.g., a computer keyboard) when treated with UVC radiation 67 according to the various embodiments. UV LEDs 66 may be mounted and positioned within an enclosure panel 64 so as to emit light toward an open side facing an object 68 to be treated. Each LED 66 emits UVC radiation, optimally at a wavelength of approximately 254 nm so as to most effectively neutralize and kill pathogens on the surface of object 68. UVC radiation 67 is emitted by each LED 66 at a projection angle, and each LED 66 may be spaced from adjacent LEDs 66 and the object 68 such that the UVC radiation 67 of each overlaps for full coverage of the surface, including any gaps or crevices, of object 68. In an embodiment, the inward-facing surface 65 between LEDs 66 may preferably be formed with a material that is highly reflective of UVC radiation, such as brushed aluminum. An opaque and sturdy material, for example, brushed aluminum, may be used to form the entire of the enclosure panel 64 as well as the inward-facing surface 65 although this is not meant as a limitation.

The embodiments described above employ rigid panels and connecting means such as hinges and slidable guides to form a piecewise flexible sanitizing apparatus. Alternatively, a panel of UV LEDs that is flexible along its length may be employed to form a continuous flexible sanitizing apparatus.

Figure 7:
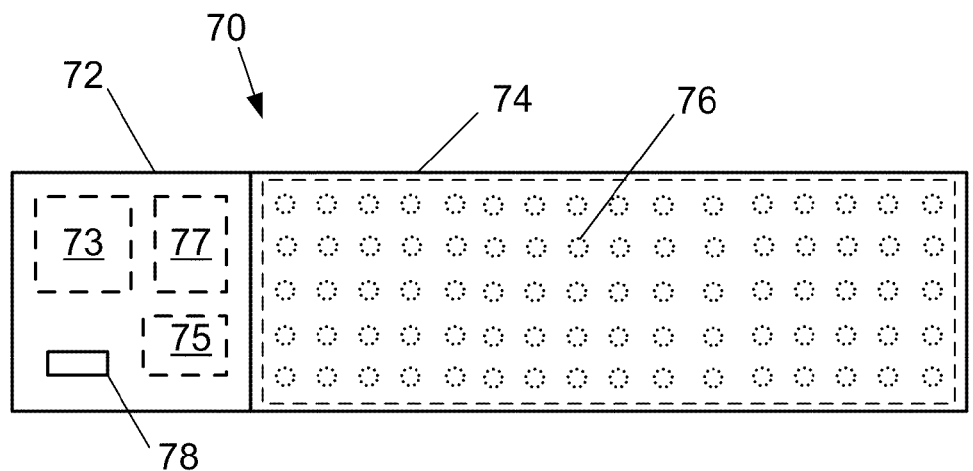
FIG. 7 illustrates a top plan view of a sanitizing apparatus having a continuous flexible panel according to an embodiment.

FIG. 7 illustrates an embodiment of a continuous flexible sanitizing apparatus 70 that has a control box 72 and pliable UV LED panel 74 with a two-dimensional array of UV LEDs 76 emitting UVC radiation for treatment of an object. Electrical control box 72 may include a power source 73, which may be any source suitable for electrically powering the plurality of LEDs, including, but not limited to, an AC power cord and appropriate transformer, a battery or set of batteries, or a fuel cell (e.g., using methanol, butane or formic acid). Control box 72 may additionally include an operating switch 78, a timing unit or circuit 75 to control the duration of sanitization, and an interlock control circuit 77 to prevent accidental operation of the apparatus 70. While illustrated as a separate, rigid box, the components of control box 72 may also be mounted or hinged to the flexible panel 74.

Figure 8:
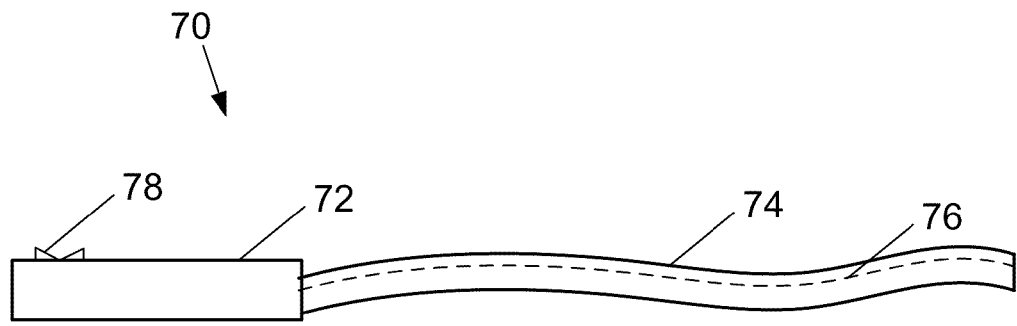
FIG. 8 illustrates a side elevation view of the sanitizing apparatus of FIG. 7.

As illustrated in FIG. 8, UV LED panel 74 is made with flexible material(s) that allow the panel 74 to be rolled or folded, and includes appropriate means to allow operation of the array of UV LEDs 76 (for example, ribbon cable wiring or UV reflective mylar). The material(s) from which panel 74 is constructed allows the panel to move and bend around the shapes of objects and surfaces. Panel 74 forms at least a backing portion of an enclosure with an open lower side to allow the array of UV LEDs 76 to emit sanitizing UVC toward an object to be treated. Panel 74 may include sufficiently rigid and dimensioned side-walls (not shown) capable of supporting the UV LED array 76 and panel 74 over an object. Alternately, panel 74 may be combined with a frame or other structure having side-walls and sufficient rigidity and dimensions to support the array 76 and opaque backing over an object, as discussed below with reference to FIG. 9-11B.

Figure 9:
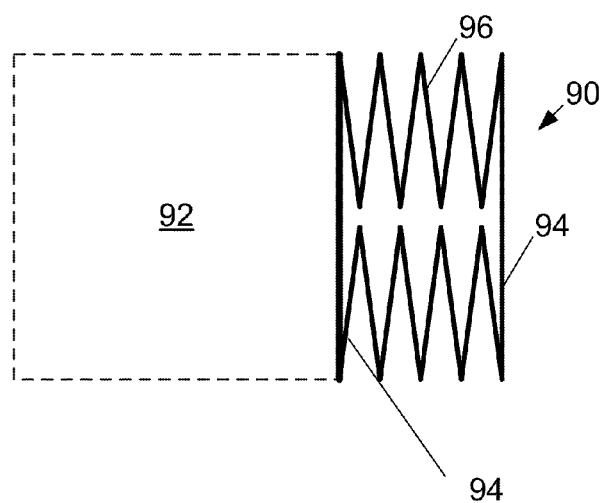
FIG. 9 illustrates a top plan view of a folding wall support for a continuous flexible panel of a sanitizing apparatus in a folded configuration for storage.

A continuous flexible sanitizing apparatus may optionally be constructed with an accompanying support structure. Such support structure may be formed as folding walls, or as a folding frame with upper members to support the enclosure panel and leg members to support the upper members. FIG. 9 illustrates a folding wall support structure 90 in a configuration for storage and transport. According to an embodiment, support structure 90 may have first and second end-walls 94 joined by a pair of side-walls 96 formed of shorter segments in an "accordion" arrangement. The support wall 90 may optionally be attached or integrated with electrical control box 92, with one end-wall 94 optionally being formed from an existing wall of control box 92. If integrated with the control box 92, the support wall 90 may fold flat against the control box 92 for storage and transport.

Figure 10:
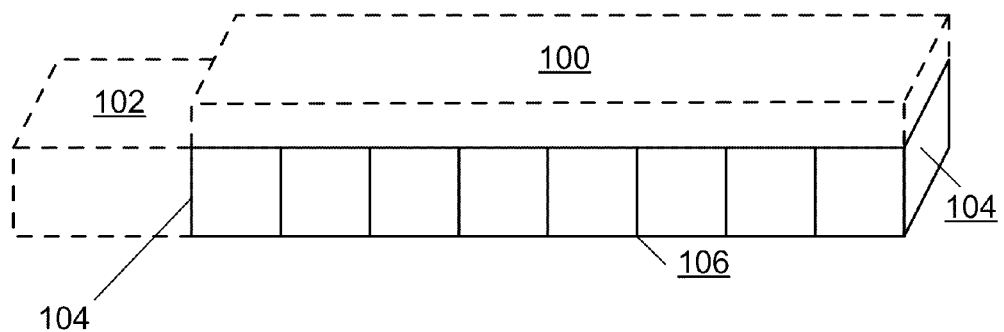
FIG. 10 illustrates a parallel projection view of a folding wall support for a continuous flexible panel of a sanitizing apparatus in an unfolded configuration for active use.

Referring to FIG. 10, the support structure 90 of FIG. 9 may be pulled out for operational use sanitizing an object. End-walls 94 and side-walls 96 may support a flexible panel 100 operated with control box 92. When using a sanitizing apparatus in such a manner, the support wall may be dimensioned to support the panel 100 in the appropriate position for treating each particular object. Optionally, means for attaching or securing the panel 100 in position on the support structure may be used as part of an interlock system for safe operation of the sanitizing apparatus so that the panel 100 will not operate when not properly secured to the support (not shown).

Figure 11A:
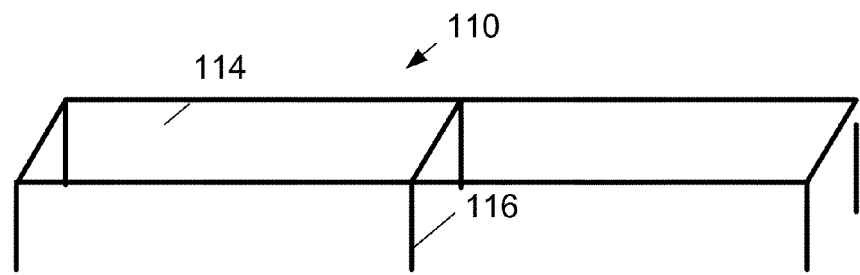
FIGS. 11A and 11B illustrate parallel projection views of alternative embodiments of a folding framework support for a continuous flexible panel of a sanitizing apparatus.
Figure 11B:
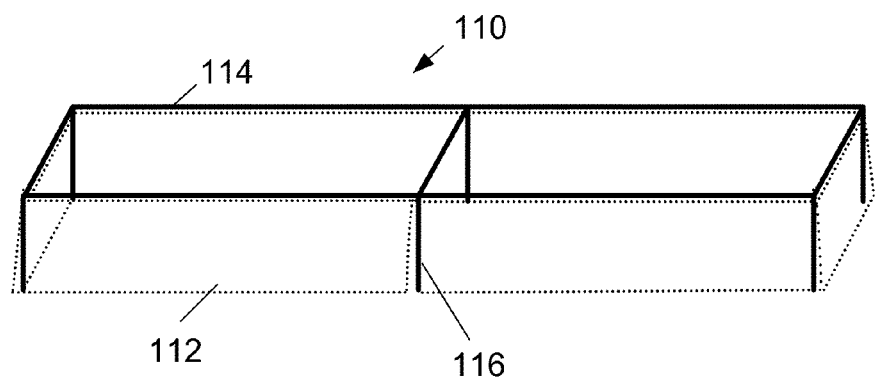

FIGS. 11A and 11B illustrate an alternative embodiment support structure for use with a flexible UV LED panel. Referring to FIG. 11A, a flexible UV LED panel (not shown) may be supported upon a folding skeletal frame 110 having upper support members 114 that contact and support the panel and leg members 116 that position the panel in the appropriate position above an object to be treated. The upper support members 114 and leg members 116 are preferably attached in a jointed manner so as to allow the frame 110 to fold for storage and transport. Referring to FIG. 11B, opaque walls 112 of any suitable material may be draped or hung from upper support members 114, stretched between leg members 116, or otherwise secured to the frame 110 to form side-walls for enclosing the UV LEDs and the object to be treated.

The side-walls 112 may be formed of rigid or pliable material which, in addition to being opaque to UV radiation, preferably are UV resistant and have an interior surface that is highly reflective of UV radiation. The frame 100 can be made of any appropriately rigid and UV resistant material, including, but not limited to, aluminum or UV resistant plastic. While leg members 114 are shown as straight, table-style legs, they may take other forms, including, but not limited to, the cross-legged form as is used for cots.

Figure 12:
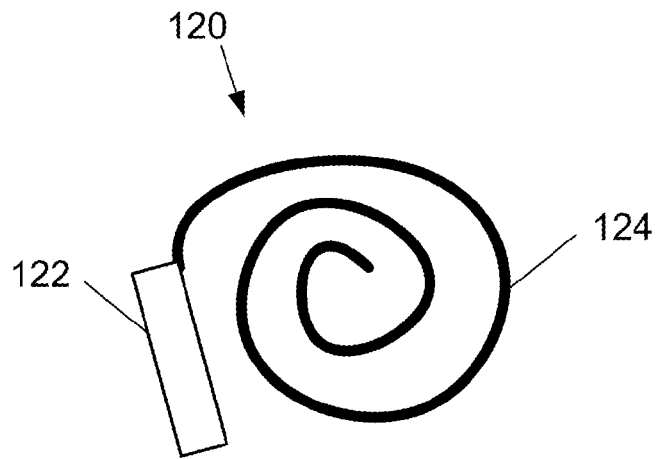
FIG. 12 illustrates a side elevation view of a continuous flexible panel of a sanitizing apparatus in a rolled storage position.
Figure 13:
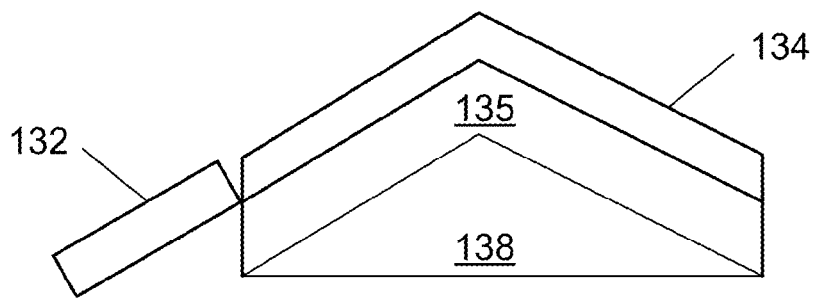
FIG. 13 illustrates a side elevation view of a continuous flexible panel of a sanitizing apparatus on a non-planer object.

Referring to FIG. 12, a sanitizing apparatus 120 having an electrical control box 122 and a flexible UV LED panel 124 according to various embodiments may be compactly stored by rolling the panel 124 toward the control box 122 or even around the control box for storage. FIG. 13 illustrates the use of a sanitizing apparatus in treating objects 138 that may not be substantially flat. In such a case, a pliable enclosure panel 134 (or a plurality of hinged enclosure panels in a piecewise flexible configuration), and, if needed, a flexible support member 135, may substantially conform to the shape of the object to be treated. Control box 132 is preferably attached to the flexible panel 134 in a hinged or similar manner to allow flexible application of the apparatus. Other embodiments of the flexible sanitizing apparatus of FIG. 12 may also have skirts of UV opaque material around the periphery of the flexible UV LED panel so that the skirt can drape down onto a surface to prevent the escape of UV illumination when sanitizing a surface or three dimensional object.

Figure 14:
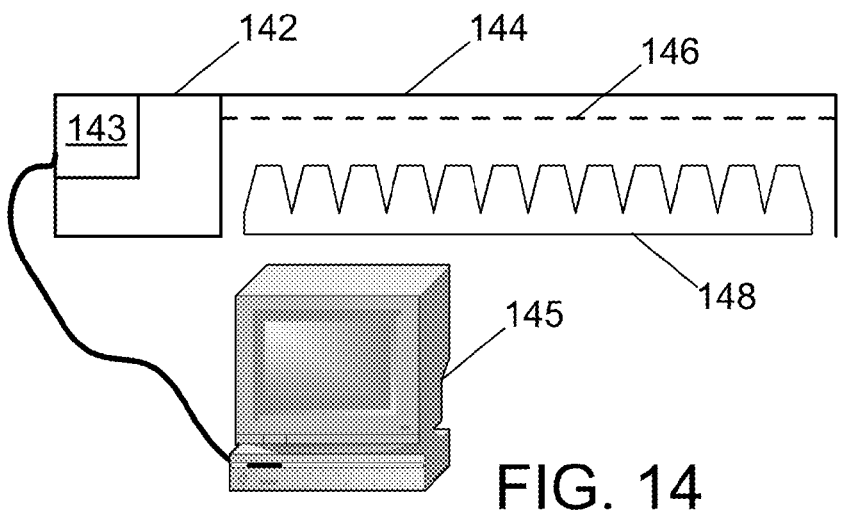
FIG. 14 illustrates a schematic view of a sanitizing apparatus with DC power supplied to the UV LEDs from a powered port of a computer according to an embodiment.

FIG. 14 illustrates an embodiment sanitizing apparatus that is particularly suited for treating the input apparatus of a computer, such as a keyboard, mouse, stylus, tablet, trackball or trackpad. In this embodiment, power source 143 is a DC input or port for receiving DC power from a powered port of a computer 145, such as the 5V power of a USB port or the up to 30V (typically 9V/12V/25V) power provided by various IEEE 1394 ports. The control box 142 may then be operated to provide power to the UV LED array 146 inside enclosure 144 to sanitize object or input device 148 with UVC radiation.

UV LEDs in the various embodiment apparatus preferably emit UVC radiation, and more preferably emit radiation at a wavelength of approximately 254 nm. It is also well known that ultraviolet radiation below 200 nm can produce small quantities of ozone by breaking up molecules of oxygen gas into free oxygen atoms that combine with nearby diatomic oxygen. Further, it is known that in sufficient concentrations, ozone has significant germicidal and sanitizing effects, for example, by disrupting and lysing cell walls thereby exposing the contents of the cell to oxidation and inactivation. Ozone gas may reach shadowed areas in keyboards, for example, beneath the keys and in any out-of-sight crevices that exist on computer input devices, where projected and reflected ultraviolet radiation may not reach. In an alternative embodiment, UV LEDs may emit a radiation having a wavelength of less than 200 nm, and preferably having a wavelength of 185 nm to accomplish optimum ozone production.

The number and spacing of the UV LEDs in the arrays shown are not meant to be limited by the drawing figures, which are only meant to be representative. Actual numbers and spacing of the UV LEDs depend on numerous factors, including, but not limited to the emission power of the LEDs, the projection angle of the UVC radiation emitted by the LEDs, the desired speed/time-required for the sanitizing, the desired cost constraints, etc. UV LEDs that emit UVC radiation in wavelengths at or below 254 nm are available from various sources, such as UVTOP250 or UVTOP255 TO-18 FW flat window LEDs available from Sensor Electronic Technology, Inc. of Columbia, S.C., or LED MOD Deep UV 22 nm/300 µW UV LEDs from Omicrom Laserage of Rodgau Germany.

In the various embodiments, electrical energy to operate the UV LEDs may be supplied by a power source and an interlock means operates to allow power to the UV LEDs when the panels are in the operational position. A switch means may be used to power the UV LEDs when activated, and the UV LEDs may be adjusted to limit active operation to a predetermined sanitizing period by a timing circuit.

Treatment of elongated surfaces described herein is provided only as an example application. Reference to elongated surfaces is not meant to be a limitation, as the various embodiments may also be used to sanitize non-elongated surfaces.

It should also be noted that the UV illumination referred to herein is not limited to constant illumination but could also be pulsed UV illumination as well.

In the various embodiments, the power source may be selected from the group consisting of fuel cells, batteries, AC power, AC power converted to DC power, and DC power, and in preferred embodiments, the power source is DC power provided by a computer port. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A sanitizing apparatus with a flexible configuration comprising:
   a two-dimensional array of ultraviolet (UV) light emitting diodes (LEDs) mounted in a flexible enclosure panel, wherein the LEDs face an open side of the flexible enclosure panel and the flexible enclosure panel is continuously flexible and pliable to allow the panel to conform to objects and be rolled or folded for storage and transport;
   a folding support structure for the flexible enclosure panel, wherein the folding support structure comprises a folding frame with upper members for supporting the flexible enclosure panel and leg members for supporting the upper members;
   a power source for providing electrical energy to operate the UV LEDs;
   an interlock means operable to allow power to the UV LEDs when the panels are in the operational position;
   a switch means for powering the UV LEDs; and
   a timing circuit operating in response to activation of the switch means to operate the UV LEDs for a predetermined sanitizing period.

2. The sanitizing apparatus of claim 1, wherein the UV LEDs emit UVC radiation.

3. The sanitizing apparatus of claim 1, wherein the UV LEDs emit sanitizing radiation at or below a wavelength of approximately 254 nm.

4. The sanitizing apparatus of claim 1, wherein the power source is selected from a group consisting of fuel cells, batteries, AC power, AC power converted to DC power, and DC power.

5. The sanitizing apparatus of claim 4, wherein the power source is DC power provided by a computer port.

6. The sanitizing apparatus of claim 1, wherein control circuitry provides both the interlock means and the timing circuit.

7. The sanitizing apparatus of claim 6, wherein the timing circuit further comprises at least one indicator whereby current operational status of the sanitizing apparatus is conveyed.

8. The sanitizing apparatus of claim 1, further comprising a control box for housing the power source, interlock means, switch means, and timing circuit.

9. The sanitizing apparatus of claim 6 wherein the flexible enclosure panel is rolled inward to the control box for transportation and storage of the apparatus.

10. The sanitizing apparatus of claim 1, wherein the support structure comprises folding walls.

11. The sanitizing apparatus of claim 1, wherein the support structure further comprises opaque, flexible side-walls.

12. The sanitizing apparatus of claim 1, wherein the support structure further comprises rigid side-walls.

13. The sanitizing apparatus of claim 12, wherein the rigid side-walls are formed from a material selected from the group consisting of aluminum and UV resistant plastic.

14. The sanitizing apparatus of claim 1 further comprising means for attaching or securing the panel on the folding support structure.

15. The sanitizing apparatus of claim 14, wherein, wherein the interlock means is configured to allow power to the UV LEDs when the panels are attached or secured to the folding support structure.

16. The sanitizing apparatus of claim 1, wherein the upper members and the leg members are attached in a jointed manner.

* * * * *